United States Patent
Fischer et al.

(10) Patent No.: US 11,401,225 B2
(45) Date of Patent: Aug. 2, 2022

(54) METHOD FOR PARTIALLY EXTRACTING BUTANOL FROM AN AQUEOUS SOLUTION COMPRISING ETHANOL AND BUTANOL

(71) Applicants: IFP Energies Nouvelles, Rueil-Malmaison (FR); Compagnie Generale des Etablissements Michelin, Clermont-Ferrand (FR)

(72) Inventors: Beatrice Fischer, Rueil-Malmaison (FR); Rejane Dastillung, Rueil-Malmaison (FR)

(73) Assignees: IFP Energies Nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 15/734,020

(22) PCT Filed: May 21, 2019

(86) PCT No.: PCT/EP2019/063137
§ 371 (c)(1),
(2) Date: Dec. 1, 2020

(87) PCT Pub. No.: WO2019/228871
PCT Pub. Date: Dec. 5, 2019

(65) Prior Publication Data
US 2021/0230087 A1    Jul. 29, 2021

(30) Foreign Application Priority Data
Jun. 1, 2018 (FR) .................................. 1854791

(51) Int. Cl.
*C07C 29/80* (2006.01)
*C07C 29/84* (2006.01)
(Continued)

(52) U.S. Cl.
CPC .............. *C07C 29/84* (2013.01); *C07C 29/80* (2013.01); *C07C 29/86* (2013.01)

(58) Field of Classification Search
CPC .......... C07C 29/80; C07C 29/82; C07C 29/84
See application file for complete search history.

(56) References Cited

U.S. PATENT DOCUMENTS 2,696,495 A * 12/1954 Carter .................... C07C 29/80
518/728
10,358,396 B2   7/2019 Dastillung et al.
2017/0291859 A1  10/2017 Dastillung et al.

FOREIGN PATENT DOCUMENTS

FR      2549043 A1    1/1985
FR      3026100 A1    3/2016
WO  2016/054706 A1    4/2016

OTHER PUBLICATIONS

International Search Report dated Jul. 11, 2019 issued in corresponding PCT/EP2019/063137 application (2 pages).

* cited by examiner

*Primary Examiner* — Medhanit W Bahta
(74) *Attorney, Agent, or Firm* — Millen, White, Zelano & Branigan, PC; Ryan Pool (57) ABSTRACT

The invention relates to a process for treating an hydroalcoholic feedstock comprising ethanol and butanol in order to produce an ethanol-rich effluent, a water-rich effluent and a butanol-rich effluent, comprising a) a water-ethanol separation step comprising a distillation column fed with said hydroalcoholic feedstock and comprising at least 14 theoretical plates, a molar reflux ratio of less than or equal to 1.2, a side withdrawal in the butanol accumulation zone and two injections of recycled streams resulting from steps b) and c); b) a demixing step comprising a section for mixing the stream withdrawn in step a) and the fraction withdrawn in (Continued)

step c), and a decanting section, the heavy phase being recycled to the distillation column of step a); c) a butanol separation step comprising a distillation column fed with the light phase resulting from step b), comprising a side withdrawal of a water/butanol/ethanol fraction recycled to the mixing section of step b) and producing a butanol-rich effluent and an ethanol-water distillate which is recycled to the distillation column of step a). This process appears to be particularly advantageous for the treatment of the hydroalcoholic effluent from the Lebedev process.

14 Claims, 2 Drawing Sheets

(51) Int. Cl.
    *C07C 29/86*    (2006.01)
    *C07C 31/08*    (2006.01)
    *C07C 31/12*    (2006.01)

METHOD FOR PARTIALLY EXTRACTING BUTANOL FROM AN AQUEOUS SOLUTION COMPRISING ETHANOL AND BUTANOL

TECHNICAL FIELD OF THE INVENTION

The invention relates to a process for treating an hydroalcoholic feedstock comprising ethanol and butanol, butanol preferably being in a small amount relatively to water and to ethanol, making it possible to partially extract the butanol and to produce a water-rich effluent, an ethanol-rich effluent and a butanol-rich effluent. This process appears to be particularly advantageous for the treatment of the hydroalcoholic effluent from the Lebedev process.

PRIOR ART

The treatment of aqueous solutions comprising ethanol is known to be difficult. This is because the separation of water and ethanol by distillation is hampered by the formation of a water-ethanol azeotrope, which limits the recovery of pure ethanol at the top of the column. The presence of butanol in the water-ethanol mixture, even in small amounts, further complicates the separation by distillation since a second azeotrope, the water-butanol azeotrope, is formed. When the mixture additionally contains other impurities, as with the water-ethanol effluent from the Lebedev process, the separation problems are aggravated.

It thus appears to be advantageous to extract the butanol, at least partially, in order to produce an ethanol-rich effluent and a water-rich effluent from hydroalcoholic solutions comprising water, ethanol and butanol, in particular when the latter is in a small amount.

Document FR 2 549 043 describes a process for fractionating an aqueous solution comprising butanol and acetone or an acetone-ethanol mixture, in order to produce an effluent comprising essentially water, a practically pure butanol effluent and an effluent rich in acetone or acetone-ethanol mixture. The process comprises a distillation section fed with the aqueous solution of butanol and acetone with which a recycled water-butanol phase has been mixed, and a second distillation section fed with the overhead distillate from the first and comprising a separation system, in particular by decantation, which makes it possible to withdraw and recycle a water-butanol phase.

However, the aqueous solution treated by the process described in the document FR 2,549,043 is relatively low in acetone, or in acetone-ethanol mixture, and does not provide any teaching on a possible transposition to the treatment of other ternary aqueous mixtures comprising butanol, in particular of hydroalcoholic mixtures comprising water, ethanol and butanol which comprise small amounts of butanol.

The present invention proposes a process for treating water-ethanol-butanol mixtures, in particular comprising small amounts of butanol, making it possible to produce a water-rich effluent, an ethanol-rich effluent and a practically pure butanol effluent.

This process appears to be particularly advantageous for the treatment of the hydroalcoholic effluent from the Lebedev process, since the separated ethanol will be more concentrated. It will therefore be able to be recycled and to serve again as reactant.

This is due to the fact that in the Lebedev process, which makes it possible to produce butadiene by conversion of ethanol, as described for example in the book "Synthetic rubber", chapter 4, W. J. Toussaint and J. Lee Marah, or more recently in the documents FR 3,026,100 and FR 3,026,101, the degree of conversion into butadiene per pass is limited. Recycling the unconverted reactants, in particular the ethanol, thus appears to be necessary in particular for economic reasons. The ethanol must therefore be separated as much as possible from the water produced (approximately 2 moles of water for one mole of butadiene), before being recycled to the reactor. This is because the water limits the reactivity and the selectivity of the reaction catalyst. It also leads to an enlargement of the equipment and an increase in the consumption of utilities.

In addition, numerous impurities, including butanol, are generated during the dehydration. Yet butanol is difficult to remove without consuming a lot of energy and polluting the water withdrawn during the treatment of the effluents in the Lebedev process. It is therefore recycled with the ethanol and returned to the reactor. A very small portion of the butanol reacts in the reactor, and the butanol accumulates over the course of recycling until the amount of transformed butanol equals the amount of butanol formed from ethanol. The transformation of the butanol effectively leads to a drop in the selectivity of the reaction catalyst of the Lebedev process, and thus to a drop in the overall yield of butadiene. Moreover, the recycled butanol carries along with it a not insignificant amount of water, which entails an increase in the size of the equipment and in the consumption of utilities, and in the difficulties in separating the ethanol and acetaldehyde reactants.

The object of the present invention is to overcome these drawbacks by providing a process for treating hydroalcoholic water-ethanol solutions comprising butanol, in particular in a small amount. In particular, the present invention provides a process for treating an hydroalcoholic feedstock comprising, in addition to water and ethanol, butanol, preferably in a small amount relatively to the water and the ethanol, by partial extraction of the butanol, so as to produce an ethanol-rich effluent and a water-rich effluent which are able to be recycled, without a significant loss of ethanol and without bringing about the problems mentioned above.

SUMMARY OF THE INVENTION

The present invention relates to a process for treating an hydroalcoholic feedstock comprising water, ethanol and butanol in order to produce an ethanol-rich effluent, a water-rich effluent and a butanol-rich effluent, comprising:
  a) a water-ethanol separation step, comprising a water-ethanol separation section comprising a distillation column comprising at least 14 theoretical plates and having a molar reflux ratio of less than or equal to 1.2, said water-ethanol separation section comprising:
    a feed of said hydroalcoholic feedstock, located at the level of or downstream of the third theoretical plate of the column,
    the side withdrawal of an hydroalcoholic solution comprising butanol in the butanol accumulation zone of the distillation column located downstream of the feed,
    an injection of the heavy phase resulting from step b), located downstream of and close to the withdrawal,
    an injection of the ethanol-water distillate resulting from step c), located upstream of the feed and close to the top of said distillation column,
    said distillation section producing, at the top of the column, an ethanol-rich effluent and, at the bottom of the column, a water-rich effluent;

b) a demixing step comprising
- a section for mixing said hydroalcoholic solution withdrawn in step a) with the water/butanol/ethanol fraction withdrawn in step c);
- a section for decanting the previous mixture, comprising a decantation tank in which the pressure is less than or equal to 6 bar absolute, said decanting section producing a heavy phase mainly comprising water and a light phase;

c) a butanol separation step, comprising a butanol distillation section comprising at least one distillation column fed with the light phase resulting from step b) and comprising a side withdrawal of a water/butanol/ethanol fraction, located on said column in a zone between the feed and the bottom of the column, said butanol distillation section producing, at the bottom of the column, a butanol-rich effluent and, at the top of the column, an ethanol-water distillate.

It has thus been discovered, surprisingly, that it is possible under certain conditions to create an accumulation of butanol in the water-ethanol distillation column. The inventors have also demonstrated that a withdrawal at this zone, combined with an elaborate system of separations and recycling operations, makes it possible to produce an ethanol-enriched effluent and a water-rich effluent, these effluents being able to be recycled. For example, in the case of the Lebedev process, the ethanol-rich effluent will be able to be recycled as a reactant to the reaction section of the Lebedev process, and the water will be able to be recycled to a washing section, thus limiting the consumption of utilities and the size of the equipment.

Advantageously, the process according to the invention makes it possible to produce an effluent which is as concentrated in ethanol as possible, without loss of ethanol and while at the same time limiting the consumption of energy.

The process according to the invention also makes it possible to recover a practically pure and therefore profitably exploitable butanol effluent and a butanol-free water effluent.

The invention is advantageously applicable to the treatment of the water-ethanol effluent from the Lebedev process. The water-ethanol effluent obtained from the reaction unit of the Lebedev process comprises, in addition to the water and the ethanol, small amounts of butanol, a by-product of the reaction for converting ethanol into butadiene. The water-ethanol distillation, in a Lebedev process, may thus be optimized by partial extraction of the butanol according to the process of the invention: the ethanol-rich effluent extracted at the top is thus more concentrated in ethanol and may be recycled to the reactor; the amount of butanol recycled is thus reduced compared to a so-called conventional Lebedev process in which the butanol is not extracted. Thus, the accumulation of the butanol in the butadiene production reactor no longer occurs, or does so less rapidly. The amount of water recycled with the ethanol-rich effluent is thus reduced as well. The energy cost of the overall Lebedev process incorporating the process according to the invention is therefore limited.

DESCRIPTION OF THE INVENTION

According to the invention, the numbering of the theoretical plates and the positioning of the various elements, in particular in the water-ethanol distillation section, with terms such as "upstream"/"downstream", are done in the direction of flow of the liquid in the distillation column, i.e. from the top to the bottom of the column.

The Lebedev process is understood to be a process for converting ethanol into butadiene, such as that described for example in the document FR 3,026,100 or FR 3,026,101.

According to the present invention, the expression "between . . . and . . . " means that the limiting values of the interval are included in the range of values which is described. Should this not be the case and should the limiting values not be included in the range described, such a clarification will be provided by the present invention.

The present invention consists of a process for treating an hydroalcoholic feedstock comprising water, ethanol and butanol in order to produce an ethanol-rich effluent, a water-rich effluent and a butanol-rich effluent, comprising:

a) a water-ethanol separation step, comprising a water-ethanol separation section comprising a distillation column comprising at least 14 theoretical plates and having a molar reflux ratio of less than or equal to 1.2, said water-ethanol separation section comprising:
- a feed of said hydroalcoholic feedstock, located at the level of or downstream of the third theoretical plate of the column,
- the side withdrawal of an hydroalcoholic solution comprising butanol in the butanol accumulation zone of the distillation column located on the distillation column downstream of the feed,
- an injection of the heavy phase resulting from step b), located downstream of and close to the withdrawal,
- an injection of the ethanol-water distillate resulting from step c), located upstream of the feed and close to the top of said distillation column,
- said distillation section producing, at the top of the column, an ethanol-rich effluent and, at the bottom of the column, a water-rich effluent;

b) a demixing step comprising
- a section for mixing said hydroalcoholic solution withdrawn in step a) with the water/butanol/ethanol fraction withdrawn in step c);
- a section for decanting the previous mixture, comprising a decantation tank in which the pressure is less than or equal to 6 bar absolute, said decanting section producing a heavy phase mainly comprising water and a light phase;

c) a butanol separation step, comprising a butanol distillation section comprising at least one distillation column fed with the light phase resulting from step b) and comprising a side withdrawal of a water/butanol/ethanol fraction, located on the butanol column in a zone between the feed and the bottom of the column, said distillation section producing, at the bottom of the column, a butanol-rich effluent and, at the top of the column, an ethanol-water distillate.

The process according to the invention preferably consists of a) the water-ethanol separation step, b) the demixing step and c) the butanol distillation step, these steps being mentioned above.

The Hydroalcoholic Feedstock

The process according to the invention applies to the treatment of hydroalcoholic feedstocks comprising water, ethanol and butanol, the butanol preferably being in a small amount relatively to the water and to the ethanol. The butanol in particular represents less than 5% mol/mol, in particular less than 2% mol/mol, more particularly less than 1% mol/mol or even less than 0.5% mol/mol, of the hydroalcoholic feedstock to be treated.

The hydroalcoholic feedstock treated by means of the process according to the invention is a liquid feedstock, preferably a solution or suspension.

The hydroalcoholic feedstock, comprising water, ethanol and butanol, may also contain other impurities, generally in proportions less than the proportion of butanol. The impurities may for example be saturated or unsaturated, or even aromatic, hydrocarbons or oxygenated, saturated or unsaturated, or even aromatic, products other than butanol.

Advantageously, when the process according to the invention is integrated into a Lebedev process, the hydroalcoholic feedstock is the water-ethanol effluent recovered at the outlet of the unit for converting ethanol to butadiene, after separation of the butadiene, washing of the liquid effluent and separation of the acetaldehyde and other light impurities.

Water-Ethanol Separation Step a)

The process according to the invention comprises a water-ethanol separation step a), comprising a water-ethanol separation section. The water-ethanol separation section comprises a distillation column comprising at least 14 theoretical plates. Advantageously, the distillation column of the water-ethanol separation section comprises between 14 and 40 theoretical plates, preferably between 20 and 35 theoretical plates and more preferably still between 24 and 33 theoretical plates.

Advantageously, the distillation column of the water-ethanol separation section includes a reflux device (or condensation device) at the top and a reboiling device at the bottom. The distillation column operates at a molar reflux ratio of less than or equal to 1.2, preferably between 0.25 and 1.2, by preference between 0.5 and 1.15 and more preferably still between 0.65 and 1.15.

The distillation column of the water-ethanol separation section is fed, preferably continuously, with said hydroalcoholic feedstock at an intermediate point of the distillation column located at the level of or downstream of the third theoretical plate (or theoretical plate number 3). The column is preferably fed with said hydroalcoholic feedstock in a zone between one-quarter and three-quarters of the total height of said column, preferably in a zone between one-third and two-thirds of the total height of said column.

The zone located between the feed and the bottom of the column is called the bottom zone.

The inventors then discovered that, under certain operating conditions of the distillation column, and with such architectural features of the column, which advantageously remain economically reasonable, a butanol accumulation zone formed, in particular in a zone located downstream of the feed.

In accordance with the invention, the water-ethanol separation section comprises a side withdrawal of an hydroalcoholic solution comprising butanol. The concentration of butanol in the withdrawn solution depends on several parameters both on the level of the feedstock composition and on the level of the characteristics of the distillation columns. However, the solution withdrawn preferably comprises at least 2% mol/mol, at least 4% mol/mol, at least 7% mol/mol, at least 10% mol/mol, of butanol, and advantageously less than 60% mol/mol, in particular less than 50% mol/mol, of butanol. This hydroalcoholic solution withdrawn also comprises at least water and possibly ethanol.

According to the invention, the side withdrawal is located in the butanol accumulation zone of the distillation column of the water-ethanol separation section, downstream of the feed, that is to say in the bottom zone of the distillation column as defined above. Advantageously, the side withdrawal is located in a zone downstream of the feed, between one-quarter and three-quarters of the height of the bottom zone, preferably between one-third and two-thirds of the height of the bottom zone. The position of the side withdrawal on the column is defined, according to the invention, in the direction of flow of the liquid in said water-ethanol distillation column, that is to say from the top to the bottom of the column.

In the water-ethanol separation step a) of the process according to the invention, the water-ethanol separation section advantageously additionally comprises two injections, making it possible to recycle the water and possibly the ethanol which are withdrawn. In particular, the water-ethanol separation section comprises:

an injection of the heavy phase resulting from the demixing step b), located downstream of and close to the side withdrawal, preferably in a zone between the side withdrawal and a third theoretical plate downstream of said side withdrawal, and an injection of the ethanol-water distillate resulting from step c), located upstream of the feed and close to the top of the distillation column, preferably in the zone of the distillation column between the theoretical plate at the top of the column at which the reflux returns and the third theoretical plate.

The devices for reflux (or condensation) at the top of the column and for reboiling at the bottom of the column which may be used in the water-ethanol separation step a) of the process according to the invention are those that are well-known to the person skilled in the art. Advantageously, the reflux device at the top of the column comprises a heat exchanger using cooling water or air, a reflux tank and a reflux pump making it possible to return the reflux to the distillation column. Advantageously, the reboiling device uses low-pressure steam.

According to the invention, the distillation section of step a) produces, at the top, an ethanol-rich effluent and, at the bottom, a water-rich effluent.

Advantageously, the ethanol-rich effluent extracted at the top of the water-ethanol column in step a) of the process according to the invention comprises at least ethanol at a content of greater than or equal to 60% mol/mol, preferably greater than or equal to 65% mol/mol and more preferably still greater than or equal to 70% mol/mol. The ethanol-rich effluent may comprise at least water. In the case where the process according to the invention is integrated into a Lebedev process, the ethanol-rich effluent may be recycled to the reaction section in which the ethanol will be consumed as reactant.

The water-rich effluent produced at the bottom of the column contains essentially water, that is to say at least 95 mol % water, by preference at least 98 mol % water, preferably at least 99 mol % water. Advantageously, the water-rich effluent contains less than 10 ppm molar, preferably less than 5 ppm molar, more preferably less than 1 ppm molar and even more preferably less than 0.1 ppm molar, of ethanol, and less than 10 ppm molar, by preference less than 5 ppm molar, preferably less than 1 ppm molar, of butanol, and more preferably is free of butanol.

Demixing Step b)

The process according to the invention comprises a demixing step b) comprising a section for mixing the hydroalcoholic solution withdrawn during step a) with a water/butanol/ethanol fraction withdrawn in step c), and a section for decanting the mixture comprising a decantation tank having a pressure of less than or equal to 6 bar absolute. The demixing step b) produces a heavy phase mainly comprising water and a light phase.

In the mixing section, the hydroalcoholic solution withdrawn in step a) in the butanol accumulation zone of the distillation column is mixed with a water/butanol/ethanol fraction withdrawn in step c). Advantageously, the water/butanol/ethanol fraction withdrawn in step c) contains little ethanol and is concentrated in butanol. Preferably, the water/butanol/ethanol fraction withdrawn in step c) comprises between 15% and 45% mol/mol, preferably between 20% and 40% mol/mol of butanol, for example between 25% and 35% mol/mol of butanol, less than 3% mol/mol of ethanol, preferably less than 1% mol/mol of ethanol, and water. Advantageously, the hydroalcoholic solution withdrawn in step a) represents between 15% and 40% mol/mol of the mixture of the mixing section of step b) of the process according to the invention, and the water/butanol/ethanol fraction withdrawn in step c) represents between 60% and 85% mol/mol of the mixture of the mixing section of step b) of the process according to the invention.

The mixing section makes it possible to obtain a mixture having a composition such as is found in the phase separation zone, also called "demixing loop", of the water/ethanol/butanol ternary diagram.

Advantageously, the pressure within the decantation tank is at a pressure of less than or equal to 6 bar absolute. More particularly, the pressure within the decantation tank is between 1 and 6 bar absolute, preferably between 1 and 4 bar absolute, more preferably between 1 and 2 bar absolute and in particular is equal to 1.5 bar absolute.

In the decanting section, under the operating conditions of the invention, the mixture obtained at the end of the mixing section of step b) of the process according to the invention will separate into two phases:
- an aqueous phase, the heavy phase, comprising mainly water, that is to say preferably at least 85 mol % water, more particularly between 85-99 mol % water, in particular between 90-98 mol % water, and
- a light phase advantageously concentrated in butanol, comprising in particular less than 15% mol/mol of ethanol, between 60% and 85% mol/mol of water and at least 5% mol/mol of butanol, by preference between 5% and 40% mol/mol of butanol, preferably between 10% and 40% mol/mol of butanol and in particular between 15% and 38% mol/mol of butanol.

The heavy phase is advantageously recycled and returned to the water-ethanol distillation column of step a), into which it is reinjected. The light phase, for its part, is recovered and treated in the following step, step c), of the process according to the invention.

In a preferred embodiment of the invention, the mixture prepared in the mixing section is cooled, for example in a heat exchanger using cooling water or air, preferably below its bubble point, for example below 95° C., in particular between 80 and 95° C., preferably between 85 and 95° C., before being sent to the decantation tank.

Butanol Distillation and Separation Step c)

The process according to the invention comprises a step c) of separating butanol comprising a distillation section and producing, at the top of the column, an ethanol-water distillate and, at the bottom of the column, a butanol-rich effluent. The distillation column of the butanol distillation section, called the butanol column according to the invention, is fed with the light phase resulting from step b) at an intermediate point between the top and the bottom. This column also comprises a side withdrawal, located in a zone between the feed and the bottom of the column, of a water/butanol/ethanol fraction.

The person skilled in the art will readily know how to dimension the distillation column used in this butanol separation step. Conventionally, the butanol separation column comprises between 10 and 30 theoretical plates, has a molar reflux of between 0.5 and 15, and is fed in the zone located in its upper half.

Advantageously, the water/butanol/ethanol fraction withdrawn comprises between 15% and 45% mol/mol of butanol, preferably 20% and 40% mol/mol of butanol, for example between 25% and 35% mol/mol of butanol, less than 5% mol/mol of ethanol, preferably less than 3% mol/mol of ethanol, more preferably less than 1% mol/mol of ethanol, and water. In accordance with the invention, the liquid withdrawn is recycled to the mixing section of step b) of the process according to the invention.

The ethanol-water distillate extracted at the top of the column in step c) of the process according to the invention comprises essentially a mixture of ethanol and water, the ethanol-water mixture representing at least 80 mol %, preferably at least 90 mol % and even more preferably at least 95 mol %, of the extracted distillate. Advantageously, the ethanol represents at least 50% mol/mol of said ethanol-water distillate, preferably at least 60% mol/mol and even more preferably at least 70% mol/mol of said ethanol-water distillate. Said ethanol-water distillate, extracted at the top of the butanol distillation column, is advantageously returned to the water-ethanol distillation column of step a) of the process according to the invention, thus making it possible to limit losses of ethanol.

The effluent extracted at the bottom of the column in the butanol distillation section of step c) of the process according to the invention is rich in butanol. It comprises in particular at least 90 mol %, preferably at least 95 mol % and even more preferably at least 97 mol % of butanol. Since this effluent is practically pure butanol, it will be able to be profitably exploited.

The butanol distillation section may comprise, in addition, a reflux device at the top, comprising for example a heat exchanger using cooling water or air, a reflux tank and a reflux pump making it possible to return the reflux to the butanol distillation column and the liquid distillate to the water/ethanol separation column of step a) of the process according to the invention. The butanol distillation section may also comprise a reboiling device at the bottom, using for example low-pressure steam.

The process according to the invention will be better understood in the light of examples 1 to 4 which follow and of the figures, which are given by way of illustration and in a non-limiting manner.

Figure 1:
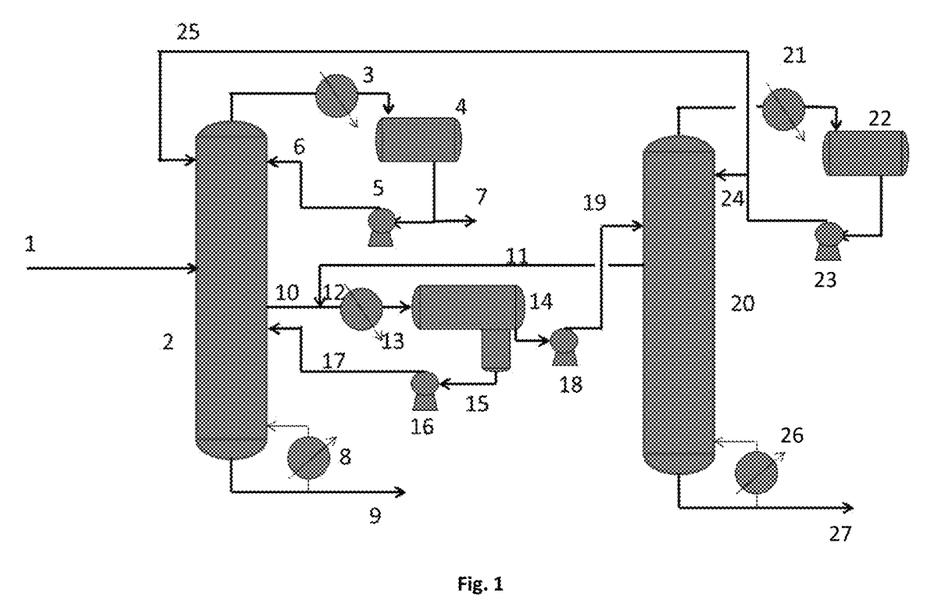
FIG. 1: Diagram of an embodiment of the process according to the invention.
Figure 2:
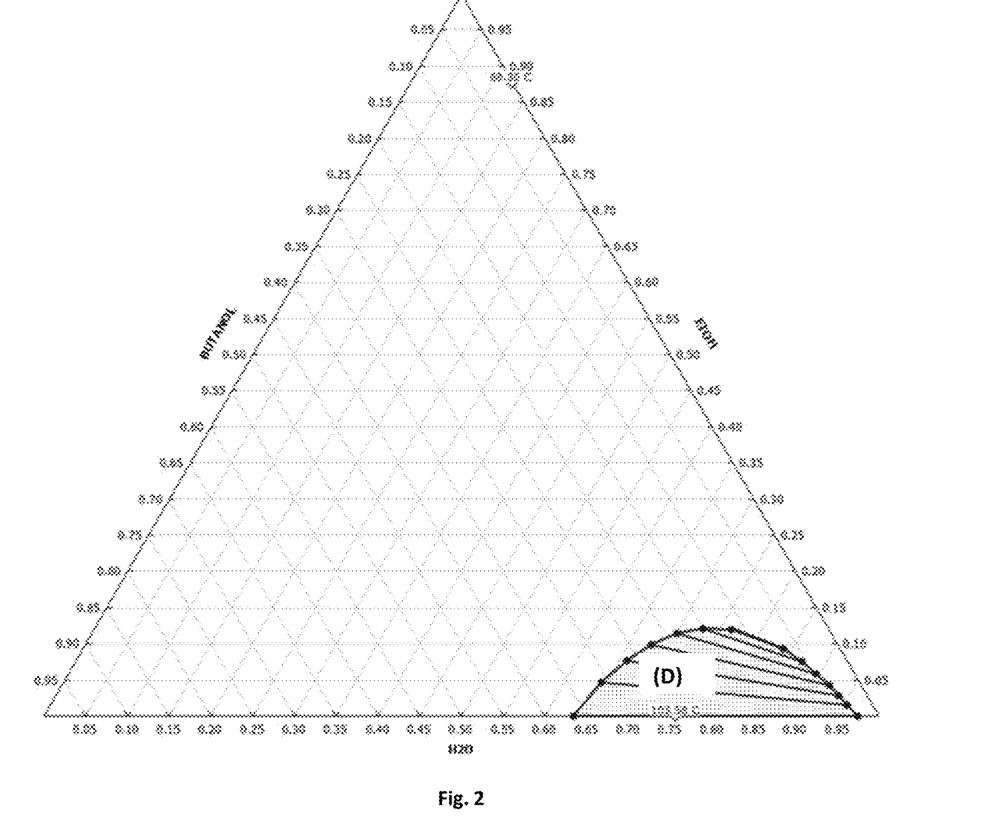
FIG. 2: water/ethanol/butanol ternary diagram obtained at a pressure of 1.5 bar, with the phase separation zone (D), called "demixing loop". At this pressure of 1.5 bar, the demixing loop (D) of the water/ethanol/butanol ternary is located at molar contents of between 60% and 98% water, between 2% and 40% butanol and less than 14 mol % ethanol.

DESCRIPTION OF FIG. 1

The hydroalcoholic feedstock feeds the water-ethanol separation column (2) via the pipe (1). The column (2) comprises a reflux (or condensation) device at the top, comprising for example a heat exchanger (3) using cooling water or air, a reflux tank (4), a reflux pump (5) returning the reflux to the column (2) via the pipe (6), and a reboiling device (8) at the bottom. The ethanol-rich effluent is extracted at the top of the column (2) via the pipe (7). The water-rich effluent is extracted via the pipe (9) at the bottom of the column (2). The column (2) also comprises a side withdrawal (10) installed in the butanol accumulation zone and two return injections, one (25) close to the top and the other (17) downstream of and close to the withdrawal.

The hydroalcoholic solution withdrawn and leaving the separation column (2) via the pipe (10) is mixed with a water/butanol/ethanol fraction coming via the pipe (11) from the butanol distillation column (20). The mixture is sent via the pipe (12), optionally via, for example, a heat exchanger (13) using water or air as the cooling fluid, into a decantation tank (14). The heavy phase leaves the decantation tank (14) via the pipe (15) and is taken, by virtue of the pump (16), via the pipe (17) to the water-ethanol separation column (2), to a theoretical plate close to and downstream of the withdrawal (10). The light phase is taken by the pump (18) through the pipe (19) to the column (20).

The distillation column (20) comprises a reflux (or condensation) device at the top, with for example a heat exchanger (21), a reflux tank (22), a reflux pump (23) returning the reflux to the column (20) via the pipe (24) and the liquid water-ethanol distillate to the separation column (2) via the pipe (25). The column (20) also comprises a reboiling device (26) at the bottom. The column (20) comprises a side withdrawal located in the zone between the feed (19) and the bottom of the column. The fraction withdrawn is sent via the pipe (11) to the mixer, with the hydroalcoholic solution from the withdrawal from the column (2). At the bottom of column (20), a butanol-rich effluent is extracted via the pipe (27).

EXAMPLES

The examples that follow are based on process simulations integrating thermodynamic data matched to experimental points (in particular binary liquid-vapor equilibrium data, liquid-liquid partition coefficient).

Example 2 illustrates the process according to the invention, in comparison to example 1 which shows a simple distillation.

Example 4 illustrates the application of the process according to the invention in a Lebedev process, in comparison to example 3 which shows the Lebedev process with a simple water-ethanol separation column.

In accordance with the invention, and in particular in the examples hereinbelow, "traces" of a compound in a stream (such as an effluent) is understood to mean a content of said compound of less than 10 ppm mol, this content being considered to be negligible in said stream, for example effluent.

Example 1 (Comparative)

An hydroalcoholic feedstock comprising water, ethanol and a low content of butanol is treated by distillation.

The characteristics of the hydroalcoholic feedstock to be treated are as follows:
- 100 tonnes/h (3773 kmol/h), at a temperature of 90° C. and a pressure of 1.8 bar abs.;
- molar composition of the feedstock: 70% water, 29.75% ethanol and 0.25% butanol (corresponding to 699 kg/h of butanol).

The hydroalcoholic feedstock feeds a distillation column comprising 22 theoretical plates, the feed being placed at theoretical plate 15 (starting from the top). The column comprises a reflux system. The column has a pressure of 1.1 bar abs. after the top condenser and 1.6 bar at the bottom and has a molar reflux ratio of 0.65 with respect to the distillate.

For this simulation, the specification for ethanol at the bottom of the column is set at 0.1 ppm molar.

An effluent (60.87 tonnes/h) comprising 70.11 mol % of ethanol, 29.30 mol % of water and 0.59 mol % of butanol is extracted at the top of the column and virtually pure water (39.13 tonnes/h), comprising 0.1 ppm molar of ethanol, is extracted at the bottom of the column. All of the butanol (699 kg/h) is found in the effluent extracted at the top, due to the formation of the butanol-water azeotrope which is lighter than water (boiling temperature of the butanol-water azeotrope=92.4° C.).

Example 2 (in Accordance with the Invention)

The same hydroalcoholic feedstock as that treated according to example 1 is treated by the process according to the invention (cf. FIG. 1).

The characteristics of the hydroalcoholic feedstock to be treated are as follows:
- 100 tonnes/h (3773 kmol/h), at a temperature of 90° C. and a pressure of 1.8 bar abs.;
- molar composition of the feedstock: 70% water, 29.75% ethanol and 0.25% butanol (corresponding to 699 kg/h of butanol).

The separation column (2) comprises 33 theoretical plates and has a reflux ratio of 0.65. It is fed with the hydroalcoholic feedstock at theoretical plate 15. At the bottom of the column, 39.85 tonnes/h of water, comprising 0.1 ppm mol of ethanol, are extracted. At the top of the column, 59.75 tonnes/h of ethanol-rich effluent comprising 72.14% mol/mol of ethanol, 27.6% mol/mol of water and 0.26% mol/mol of butanol is extracted. 100 kmol/h (2.6 tonnes/h) are withdrawn at plate 26. The liquid withdrawn contains 79% mol/mol of water, 7.67% mol/mol of butanol and 13.33% mol/mol of ethanol.

The liquid withdrawn from column (2) is mixed with a fraction (11) withdrawn on column (20) (withdrawn between the feed and the bottom) and having a flow rate of 186 kmol/h (6.8 tonnes/h) and a molar composition of 67.06% water, 32.82% butanol and 0.13% ethanol. The mixture is then cooled from 102° C. to 92° C. in a heat exchanger (13).

The mixture is decanted in the tank (14) at a pressure of 1.05 bar absolute. The stream (15) of the heavy phase returning to the column (2), at theoretical plate 27, has a flow rate of 78 kmol/h (1.6 tonnes/h) and a molar composition of 95.41% water, 1.83% ethanol and 2.76% butanol. The light phase comprising 62.12% mol/mol of water, 32.03% mol/mol of butanol and 5.85% mol/mol of ethanol is sent, at a flow rate of 208.7 kmol/h (7.85 tonnes/h), to column (20).

The molar reflux ratio of column (20) relatively to its feedstock is 1.2.

At the top of column (20), 16.39 kmol/h (0.64 tonne/h) are returned via pipe (25) onto theoretical plate 3 of column (2): the molar composition of the distillate extracted at the top of column (20) is 72.92% ethanol, 25.55% water and 0.53% butanol.

Butanol having a purity of 99.99% mol/mol is extracted at the bottom of column (20).

Thus, the process according to the invention makes it possible to recover 400 kg/h (5.4 kmol/h) of butanol at the bottom of column (20), relatively to the 699 kg/h of butanol present in the feedstock feeding column (2).

Overall, compared to a simple distillation as illustrated in example 1, the process makes it possible to recover an ethanol effluent which is more concentrated in ethanol (72.14 mol % instead of 70.11% in example 1), with two times less butanol (0.26 mol % of butanol instead of 0.59 mol % of butanol in the ethanol effluent illustrated in example 1). The process according to the invention also makes it possible to recover, in this case, more than half of the butanol entering the process in the form of virtually pure, and therefore profitably exploitable, butanol.

Example 3 (Comparative)

This example shows the simulation of the Lebedev process described in document FR 3,026,100 in which the water-ethanol effluent is treated by simple distillation in a separation column.

The production unit is fed with 48 670 kg/h of feedstock comprising 93.3% by weight of ethanol and 6.7% by weight of water.

In this Lebedev process, 18 850 kg/h of product comprising 99.84% butadiene are produced, consuming a total of:
  201.3 t/h of steam (117.4 MW)
  86.81 MW of furnace heating
  8377 kW of electricity
  21 t/h of process water
  25 120 m$^3$/h of cooling water.

More particularly, the water-ethanol separation column of the simulated Lebedev process comprises 30 theoretical plates and has a molar reflux ratio of 1. It is fed at theoretical plate 15 with the water-ethanol effluent obtained from the butadiene production/separation unit of the overall process at a flow rate of 167.6 tonnes/h. This water-ethanol effluent has the following molar composition on entry into the separation column:
  25.39 mol % of ethanol;
  73.74 mol % of water;
  0.23 mol % of butanol (corresponding to 1.1 tonnes/h of butanol);
  0.51 mol % of acetic acid;
  0.13 mol % of other impurities.

At the bottom of this separation column, the effluent extracted has the following molar composition: 99.09% water, 0.86% acetic acid and 0.05% other impurities (traces of ethanol and butanol).

At the top of the separation column, 96.38 tonnes/h are extracted, with the following molar composition:
  62 mol % of ethanol;
  37.2 mol % of water;
  0.55 mol % of butanol (corresponding to 1.1 tonnes/h of butanol);
  0 mol % of acetic acid;
  0.25 mol % of other impurities.

The reboiler of the water-ethanol separation column consumes 58.4 MWh/h, that is to say for example 100 tonnes/h of low-pressure steam, and the cooling of the column requires 59.6 MWh/h, that is to say for example the circulation of 6921 tonnes/h of cooling water.

Thus, all of the butanol entering the separation column is extracted at the top of the column with the ethanol effluent intended to be recycled to the butadiene production unit, leading to problems with the accumulation of butanol in the reactors and a loss of activity and selectivity of the butadiene conversion catalysts.

It is also apparent that the steam consumption of this separation column represents approximately half of the total consumption of the overall process (100 tonnes/h of steam compared to a total of 201), without the butanol being separated.

Example 4 (According to the Invention)

This example simulates the Lebedev process as in the previous example, but into which the treatment process (cf. FIG. 1) according to the invention has been inserted in place of the simple separation column.

The same feedstock as that in example 3, comprising 93.3% by weight of ethanol and 6.7% by weight of water, feeds the production unit at a flow rate of 48 670 kg/h. The unit for treating the water-ethanol effluent obtained from the conversion unit comprises the separation section (step a) of the process according to the invention), the mixing and decanting sections (step b) of the process according to the invention) and the butanol separation section (step c).

The water-ethanol separation column (2) comprises 30 theoretical plates and has a molar reflux ratio of 0.779. It is fed with the water-ethanol effluent obtained from the conversion unit at theoretical plate 15. In this case, the water-ethanol effluent at the inlet to the separation column (2) has a flow rate of 158.5 tonnes/h and the following molar composition:
  Ethanol: 29.94 mol %;
  Water: 72.27 mol %;
  Butanol: 0.17 mol % (corresponding to 787 kg/h of butanol);
  Acetic acid: 0.53 mol %;
  Other impurities: 0.09 mol %.

A water-rich effluent is extracted at the bottom of the column (2). It has the following molar composition:
  Ethanol: traces;
  Water: 99.15 mol %;
  Butanol: traces;
  Acetic acid: 0.85 mol %;
  Other impurities: traces.

The product extracted at the top of column (2) is recycled to the reactor for converting ethanol into butadiene at a flow rate of 88.69 tonnes/h. It has the following molar composition:
  Ethanol: 71.02 mol %;
  Water: 28.40 mol %;
  Butanol: 0.33 mol % (corresponding to 574 kg/h of butanol);
  Acetic acid: 0.0 mol %;
  Other impurities: 0.25 mol %.

The separation column also comprises a side withdrawal at theoretical plate 23 of a liquid at a flow rate of 3772 kg/h (that is to say 161.5 kmol/h) and comprising 4.6 mol % of butanol (that is to say a flow rate of butanol of 550 kg/h), 8.99 mol % of ethanol, 85.84 mol % of water, 0.57 mol % of acetic acid and traces of impurities.

The liquid withdrawn on the separation column (2) is mixed with the fraction withdrawn from column (20). The mixture is then cooled to 92.5° C. in a heat exchanger (13) and then sent to a decantation tank (14) having a pressure of 1.05 bar.

The heavy phase withdrawn from the decanting tank has a flow rate of 2776 kg/h and a molar composition of 95.35% water, 1.16% ethanol, 2.88% butanol and 0.6% acetic acid (traces of impurities). This stream is sent to plate 24 of column 2.

The light phase withdrawn from the decanting tank has a flow rate of 20 040 kg/h and a molar composition of 62.17% water, 3.71% ethanol, 33.39% butanol and 0.74% acetic acid (traces of impurities). This stream is the feedstock for column (20).

Column (20) includes 22 theoretical plates and is fed at plate 9. The molar reflux ratio for this column (20) is 11.76.

A side withdrawal is carried out on column (20) at theoretical plate 17. The fraction withdrawn from column (20) is sent to the mixing section at a flow rate of 19.05 tonnes/h (that is to say 502 kmol/h). Its molar composition is: 63.63% water, 1.31% ethanol, 34.31% butanol and 0.76% acetic acid (traces of impurities).

The distillate extracted at the top of column (20) is returned to the water-ethanol separation column (2) at a flow rate of 780 kg/h. Its molar composition is: 60.84% ethanol, 36.34% water, 2.82% butanol and traces of acetic acid (traces of other impurities).

The effluent at the bottom of column (20) is extracted at a flow rate of 218 kg/h and has the following molar composition:
Ethanol: traces
Water: traces
Butanol: 97.15 mol %
Acetic acid: 2.85 mol %
Other impurities: traces.

The consumption of utilities is 43.88 MW for the reboiling in column (2) and 3.28 MW for the reboiling in the butanol separation column (20), i.e. a total of 47.16 MW.

Table 1 below summarizes the results of the unit for treating the water-ethanol effluent from the Lebedev process using the treatment process according to the invention and compares these results to those of the treatment unit comprising a simple distillation column (comparative example 3).

TABLE 1

Results of the units for treating the water-ethanol effluent using the process according to the invention or using a simple distillation column (comparative example 3).

| | | With the process according to the invention | With a simple distillation |
|---|---|---|---|
| Unit feedstock | Total flow rate (tonnes/h) | 158.5 | 167.6 |
| | BuOH flow rate (tonnes/h) | 0.787 | 1.1 |
| Effluent extracted at the top of the water-ethanol column and recycled | Flow rate (tonnes/h) | 88.69 | 96.38 |
| | EtOH content (mol %) | 71.02 | 62 |
| | Water content (mol %) | 28.40 | 37.2 |
| | Butanol content (mol %) | 0.33 | 0.55 |
| | Flow rate of recycled butanol (tonnes/h) | 0.574 | 1.1 |
| Butanol-rich effluent extracted | | 218 kg/h at 97.15 mol % BuOH | NA |
| Energy consumption for the reboiling (MW) | | 47.16 | 58.4 |

When the process according to the invention is used in the unit for treating the water-ethanol effluent from the Lebedev process, it is apparent that:
the amount of hydroalcoholic feedstock (158.5 tonnes/h) feeding the water-ethanol separation column (2) is reduced compared to the amount of feedstock (167.6 tonnes/h) for a simple separation column such as that of example 3. This is explained by a reduced amount of water recycled with the ethanol into the unit for the conversion reaction to butadiene (28.40 mol % of water compared to 37.2 mol %);

the ethanol-rich effluent, recovered at the top of the water-ethanol separation column (2), has a lower flow rate (88.69 tonnes/h compared to 96.38 tonnes/h);

the ethanol-rich effluent, recovered at the top of column (2), contains more ethanol (71.02 mol %) with a gain of more than 10 points compared to the composition of the ethanol effluent in the case of a simple distillation (62 mol %);

a portion of the butanol entering the treatment unit is extracted in the case of the process according to the invention, whereas all of the butanol is recycled to the reactor in the case of a simple distillation. The purity of the butanol, recovered at the bottom of column (20), is very satisfactory and makes it possible to envisage profitable exploitation of the butanol (for example marketing of the butanol, possibly as bio-based butanol);

the consumption of utilities for the reboiling is reduced by 20% in the case of the process according to the invention (47.16 MW) compared to the case of simple distillation (58.4 MW).

In the case of the integration of the treatment process according to the invention into the Lebedev process, the overall consumption of utilities for the entire Lebedev process are, in comparison with those obtained for the process described in example 3:
181.4 t/h of steam (i.e. 105.8 MW), that is to say a reduction of 10%; 81 MW of furnace heating, that is to say a reduction of 6.7%;
8168 kW of electricity, that is to say a reduction of 2.5%;
21 t/h of process water (unchanged);
22 125 m$^3$/h of cooling water, that is to say a reduction of 12%.

It is clearly apparent that savings on utilities can be made in the case of the Lebedev process including the treatment process according to the invention.

Moreover, by including such a treatment process in the Lebedev process, insofar as the butanol is partially extracted, the catalytic performance will be able to be improved. A reduction in the amount of heavy impurities resulting from the degradation of the butanol and also a limitation of the effluents which could demix in the process will also be able to be observed.

In the case of the Lebedev process integrating the treatment process according to the invention, the fact that the ethanol-rich effluent recycled to the reaction unit of the Lebedev process is more concentrated in ethanol (less water and less butanol) makes it possible to save on utilities in the reaction sections (saving in the vaporization of the feedstock) and during the treatments downstream of the reaction sections (saving in the distillations and washing operations) compared to the Lebedev process without the treatment process according to the invention.

The invention claimed is:

1. A process for treating a hydroalcoholic feedstock comprising water, ethanol and butanol in order to produce an ethanol-rich effluent, a water-rich effluent and a butanol-rich effluent, the process comprising:
step a) separating water and ethanol in an area comprising a water-ethanol separation section comprising a distillation column comprising at least 14 theoretical plates and having a reflux ratio of less than or equal to 1.2, said water-ethanol separation section additionally comprising:
a feed of said hydroalcoholic feedstock, located at the level of or downstream of a theoretical plate number 3 and forming a bottom zone located between the feed and the bottom of the column and a top zone between the feed and the top of the column, a side withdrawal of a hydroalcoholic solution comprising butanol in the butanol accumulation zone of the distillation column located downstream of the feed, an injection of a heavy phase resulting from step b), into the distillation column in a zone between the side withdrawal and a third theoretical plate downstream of the side withdrawal which is positioned in the bottom zone, an injection of an ethanol-water distillate resulting from step c), into the distillation column upstream of the feed and in a zone bounded upstream by the top zone of the column where the reflux returns and the theoretical plate number 3, said distillation section producing, an ethanol-rich effluent at the top zone of the column and, a water-rich effluent at the bottom zone of the column;

step b) demixing wherein said demixing is provided in an area comprising:

a section for mixing said hydroalcoholic solution withdrawn in step a) with a water/butanol/ethanol fraction withdrawn in step c) to form a mixture;

a section for decanting the mixture, comprising a decantation tank in which the pressure is less than or equal to 6 bar absolute, said decanting section producing the heavy phase mainly containing water and a light phase;

step c) separating butanol in an area comprising a butanol distillation section comprising at least one distillation column fed with the light phase resulting from step b) and comprising a side withdrawal of the water/butanol/ethanol fraction, located on said column in the bottom zone, said butanol distillation section producing, a butanol-rich effluent at the bottom of the column and, the ethanol-water distillate at the top of the column.

2. The process as claimed in claim 1, in which the butanol is present in the hydroalcoholic feedstock but represents less than 5% mol/mol of the hydroalcoholic feedstock.

3. The process as claimed in claim 1, in which the distillation column of the separation section of step a) comprises between 20 and 35 theoretical plates.

4. The process as claimed in claim 1, in which the distillation column of the separation section of step a) has a molar reflux ratio of between 0.5 and 1.15.

5. The process as claimed in claim 1, in which the distillation column of the separation section of step a) is fed with said hydroalcoholic feedstock in a zone between one-third and two-thirds of the total height of said column.

6. The process as claimed in claim 1, in which the side withdrawal of step a) is located in a zone between one-third and two-thirds of the height of the bottom zone of the column, said bottom zone being the zone located between the feed and the bottom of the column.

7. The process as claimed in claim 1, in which the hydroalcoholic solution withdrawn in step a) represents between 15 and 40% mol/mol of the mixture of the mixing section of step b).

8. The process as claimed in claim 1, in which the pressure in the decantation tank is between 1 and 2 bar absolute.

9. The process as claimed in claim 1, in which the mixture obtained from the mixing section of step b) is cooled to a temperature between 80 and 95° C., before being sent to the decantation tank.

10. A Lebedev process comprising:

treating a hydroalcoholic feedstock utilizing the process of claim 1, wherein the hydroalcoholic feedstock is a water-ethanol and butanol effluent obtained from the reaction unit of said Lebedev process and the ethanol-rich effluent produced in step a) is recycled to the reaction unit.

11. The process of claim 2, wherein the butanol is present in the hydroalcoholic feedstock but represents less than 2% mol/mol.

12. The process of claim 2, wherein the butanol is present in the hydroalcoholic feedstock but represents less than 1% mol/mol.

13. The process of claim 2, wherein the butanol is present in the hydroalcoholic feedstock but represents less than 0.5% mol/mol.

14. The process of claim 4, wherein the distillation column of the separation section of step a) has a molar reflux ratio of between 0.65 and 1.15.

* * * * *